United States Patent [19]

Galliher

[11] Patent Number: 4,999,422
[45] Date of Patent: Mar. 12, 1991

[54] CONTINUOUS METHOD OF REFOLDING PROTEINS

[75] Inventor: Parrish M. Galliher, Acton, Mass.

[73] Assignee: Biogen, N.V., Boston, Mass.

[21] Appl. No.: 181,963

[22] Filed: Apr. 15, 1988

[51] Int. Cl.⁵ .......................... C07K 3/12; C07K 3/28; C07K 15/26; C07K 15/08

[52] U.S. Cl. .................................... 530/351; 530/350; 530/383; 530/399; 530/422; 530/427; 435/69.1; 435/69.51; 435/69.4

[58] Field of Search ............... 530/427, 422, 412, 351, 530/350, 383, 399; 435/813, 68, 69.4; 424/85.5, 85.6, 85.7

[56] References Cited

U.S. PATENT DOCUMENTS

| | | | |
|---|---|---|---|
| 3,547,900 | 12/1970 | Dienst et al. | 260/112 |
| 4,017,600 | 4/1977 | Stewart et al. | 424/85 |
| 4,427,658 | 1/1984 | Maubois, Jr. et al. | 424/177 |
| 4,511,502 | 4/1985 | Builder et al. | 530/417 |
| 4,828,989 | 5/1989 | Prior et al. | 435/68 |

FOREIGN PATENT DOCUMENTS

| | | | |
|---|---|---|---|
| 0114506 | 8/1984 | European Pat. Off. | 435/68 |
| 59-82094 | 5/1984 | Japan . | |
| 0999256 | 7/1965 | United Kingdom | 435/813 |

*Primary Examiner*—Margaret Moskowitz
*Assistant Examiner*—Keith C. Furman
*Attorney, Agent, or Firm*—James F. Haley, Jr.; Leon R. Yankwich

[57] ABSTRACT

A process is disclosed for continuously treating a solubilized protein solution containing a protein unfolded to some degree, in a small volume continuous flow reactor, to obtain the protein in a conformation exhibiting the protein's characteristic biological activity by continuously diluting out the solubilizing agent, while continuously withdrawing the refolded protein. The continuous process may be carried out using deionized water as a diluent, rather than buffer solutions.

10 Claims, 1 Drawing Sheet

CONTINUOUS METHOD OF REFOLDING PROTEINS

This invention relates to a process for treating a solubilized protein to refold the protein to a conformation such that the protein is biologically active. More particularly, the invention relates to a process for refolding a solubilized protein, which is unfolded to some degree, through continuous, small scale dilutions using a small volume continuous flow reaction vessel, rather than using conventional batch dilution techniques. In the most preferred embodiment, the diluent is deionized water.

BACKGROUND OF THE INVENTION

Recent developments in recombinant DNA procedures have created special problems in the purification of proteins from cell extracts and particularly in recovering cell proteins in useable forms. These recent developments in recombinant DNA procedures allow the synthesis of foreign proteins in host microorganisms, such as bacterial, yeast and animal cells. This is accomplished by transforming a host cell with a DNA sequence coding for the expression of a foreign protein. When the level of expression of the DNA sequence in a transformed host cell is high, a large amount of the foreign protein is produced within the host cell. Typically the cell sequesters most of these foreign proteins in inclusion bodies within the cytoplasm of the cell. The proteins sequestered in this manner are in the form of insoluble protein aggregates primarily composed of many monomers of the foreign protein bound together, typically through hydrophobic interactions.

The formation of these inclusion bodies containing the foreign protein normally would be helpful for the purification of the protein, because the inclusion bodies consist primarily of the foreign protein aggregates and, being insoluble, are readily isolated from the cell. However, in this insoluble, aggregate form, the protein is typically not in its preferred biologically active conformation such that the protein is capable of effecting its intended in vivo physiological responses.

Thus, purification of the protein in a biologically active form from the insoluble aggregates requires a means of solubilizing the protein aggregates in such a way to preserve, or to enable ultimate recovery of, the protein in a biologically active conformation.

The initial step in recovering the inclusion body contained proteins from transformed cells generally involves breakage of the cells through a combination of enzyme treatment and mechanical disruption to release the inclusion bodies. Because the protein aggregates contained in the inclusion bodies are insoluble, centrifugation of the resulting cellular material produces a membrane pellet containing a significant amount of the foreign protein, still in the form of insoluble aggregates. The pellet also contains lipids, lipopolysaccharides and traces of nucleic acid.

The next step typically used to recover the protein is to "solubilize" the insoluble protein aggregates. This may be accomplished by treating the membrane pellet with a strong chaotrope, e.g., guanidine hydrochloride, to denature and dissolve the protein. See, e.g., U.S. Pat. Nos. 4,511,502, 4,512,922, 4,518,526 and 4,620,948. "Solubilization" may also be effected using less stringent chatropes, e.g., urea, that "solubilize" but do not completely denature the desired protein. See, e.g., U.S. Pat. No. 4,652,630. If the protein contains more than one cysteine, it will usually have disulfide linkages in its structure. For these proteins, treatment with a reductant such as, e.g., dithiothreitol (DTT) to cleave the disulfide bonds may also be used during "solubilization" of the protein from the inclusion body. These chaotropes and reductants either alone or in combination will be referred to herein as "solubilizing agents".

When a protein is produced in vivo, its amino acid chains are "folded" into thermodynamically preferred three dimensional structures. Every protein has a unique folded conformation which is the most thermodynamically stable. This conformation is the protein's "native" conformation and gives the protein its characteristic biological activity. Factors influencing the protein's conformation ("conformation factors"), include steric interactions, charge interactions, Van der Waal forces, hydrophobic interactions and disulfide bond linkages between cysteine groups, if those are present in the protein.

Solubilizing agents disrupt the protein's conformation factors and "unfold" the protein to a degree that depends on the strength of the solubilizing agent. The greater the extent of the unfolding, the less degree of biological activity the protein likely displays. The resulting solubilized protein solution obtained after one or more of the above-described "solubilizations", thus comprises the foreign protein in some stage of unfolding, depending on the particular solubilizing treatment employed. To obtain a biologically active conformation of the desired protein, it must thus be "refolded". The solubilized protein solution also contains other soluble or solubilized phospholipids, lipopolysaccharides, proteins, and nucleic acids from the inclusion body and insoluble cellular debris. These must, of course, be removed either before or after refolding of the foreign protein.

A typical refolding method used to refold solubilized proteins involves diluting out the solubilizing agent with a large volume of diluent, generally a buffer. When the concentration of solubilizing agent is reduced to a dilution level where the protein's conformation factors begin to reassert themselves, the protein hopefully spontaneously refolds into a soluble, biologically active conformation. Depending on the protein, once this "optimal dilution level" is reached, refolding begins to occur within seconds or may take several minutes or longer.

Typically, the dilution is carried out in one step by mixing the solubilized protein solution with a diluent in an amount necessary to reach the optimal level of dilution. This dilution method is known as a "batch" dilution, drawing its name from the procedure of adding the diluent in one operation to the solubilized protein solution. Utilization of this batch method for refolding a solubilized protein has several disadvantages which are magnified when the refolding is carried out with the large volumes used in commercial scale purification procedures.

Because a solubilized protein solution generally has to be diluted with many times its volume of diluent to achieve at least some degree of refolding, the total volumes being handled at once in commercial protein purification methods can be very large, e.g., 5000 liters. This necessitates the use of large mixing chambers and special holding tanks and associated support systems, along with large amounts of chemicals for preparing the buffer diluents. Additionally, refolding proteins in large volumes by batch dilution may cause some reaggregation of the proteins, probably because the solutions at least initially present in batch dilutions are not homogeneous. This may result in a lowered net yield of refolded protein.

The non-homogenous solutions in batch dilutions result from the difficulty in rapidly achieving "ideal" mixing conditions in large volume solutions, i.e., conditions resulting in a homogenous solution without concentration gradients in solution. Ideal mixing conditions are a function of a solution's "mixing time". Mixing time is the time needed for the molecules in a droplet added to a solution to be dispersed evenly throughout the solution. Variables affecting mixing time include the volume of solution being mixed, size and configuration of the mixing chamber, the characteristics of the mixing device, and the location in the mixing chamber where the solutions are added. The larger the volumes of solution and the larger the size of the reaction vessel, the longer the mixing time and thus the longer that the mixture, e.g., of solubilized protein solution and diluent will not be homogenous.

A non-homogenous solution will have concentration gradients. These concentration gradients produce concurrent ionic strength variations in solution, which interfere with the charge interactions determining the conformation of the protein. Proteins refold into their native conformation through the repulsion and attraction of charges on their amino acid side chains and through the formation of cysteine-cysteine disulfide bonds. Variations in pH and ionic strength in turn may vary the charges and the attractive and repulsive forces, causing the protein to refold incorrectly or interact improperly with other nearby molecules. This phenomenon may decrease the net yield of correctly refolded proteins obtainable from a given volume of solubilized protein solution. Additionally, the use of large volumes makes it difficult to precisely control pH and ionic strength, resulting in less repeatable, less uniform yields. These problems have seriously hampered efforts to produce pure proteins in quantity at acceptable cost.

Conventional dilution procedures try to decrease the effect of these problems by using buffers as diluents to enhance ionic stability, the theory being that because buffers maintain isotonic concentrations, they will stabilize solution ionic strength and thus small concentration gradients will have less of an effect on solution ionic strength.

Conventional dilution methods do not utilize water as a diluent because it was commonly thought that water has no buffering effect. It would thus cause ionic strength variations in solution until completely mixed, thus causing excessive reaggregation of the proteins, and substantially decreasing the obtainable yield of a biologically active, soluble refolded protein (e.g., see U.S. Pat. No. 4,620,948). We have unexpectedly found that deionized water can be used as a diluent by using small volume mixing to maximize "ideal" mixing conditions.

SUMMARY OF THE INVENTION

This invention solves the problems referred to above by providing a continuous process for treating a "solubilized" protein, in small volumes, by continuous dilution, in order to obtain the protein in a biologically active conformation. Specifically, this invention provides a continuous dilution process for treating a "solubilized" protein in a continuous flow reaction vessel, to cause the protein to refold to a biologically active conformation. A further aspect of this invention enables the use of deionized water as a diluent in the continuous dilution process disclosed by this invention. Still further, the continuous dilution process of this invention can be scaled to accommodate the high volumes used in commercial protein production, while maximizing ideal mixing conditions.

One protein advantageously treated according to the processes of this invention is immune or gamma interferon (IFN-$\gamma$). The purified, refolded and biologically active gamma interferon produced according to this invention may be utilized in the therapeutic treatment of viral infections, tumors or cancer, as well as in immunomodulation applications and methods. This invention provides a particularly effective means to purify human IFN-$\gamma$ produced in genetically engineered transformant cells, in a stable, biologically active conformation.

Any other protein which can be refolded in batch dilution methods can be refolded in accordance with this invention. Such proteins include proteins such as insulin, proinsulin, bovine pancreatic ribonuclease, lysozyme, bovine pancreatic trypsin inhibitor, other interferons, rennin, plasminogen activator, prolactin, human $\alpha$-1 trypsin inhibitor, Factor VIII, and the like [Pigiet et al., European Patent Application 208,539.]

DETAILED DESCRIPTION OF THE INVENTION

Figure 1:
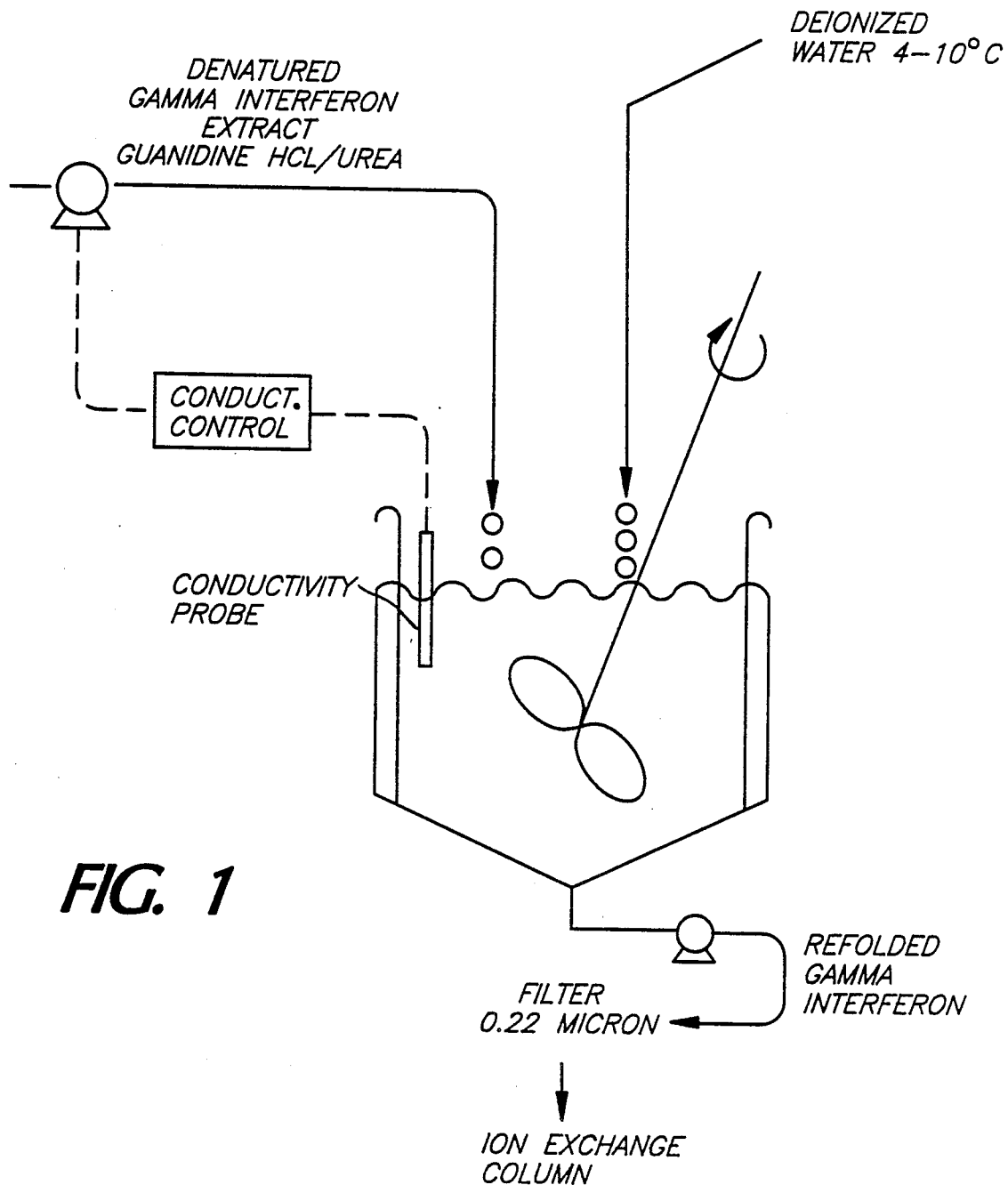
FIG. 1 is a schematic diagram of a continuous flow reaction vessel used in this invention.

In accordance with this detailed description, the following definitions apply:

"Host cell" includes unicellular cells such as bacteria and yeast, or other suitable cells such as animal and plant cells which have been transformed to express a foreign protein.

"Foreign proteins" are proteins coded for by a non-native or heterologous segment of DNA not normally found in the host cell.

"Inclusion bodies" refers to the insoluble cytoplasmic aggregates containing foreign proteins often found in transformed cells.

The "conformation" of a protein describes the three dimensional structure of the protein's amino acid chains.

"Conformation factors" are forces influencing a protein's conformation, and include steric interactions, charge interactions, hydrophobic interactions and disulfide bond linkages.

"Biological activity" means that the protein is in a conformation such that it is capable of effecting its intended in vivo physiological response, and exhibits activity in biological assays.

"Solubilizing agents" are chaotropes such as guanidine hydrochloride or urea and also include reductants such as DTT, or mixtures thereof. These solubilizing agents to at least some extent denature or unfold proteins, thus rendering them soluble.

A "solubilized protein solution" refers to a solution formed by mixing a protein with a solubilizing agent such that the resulting protein solution comprises the protein in some stage of unfolding, depending on the particular solubilizing agent employed.

"Solubilized protein" refers to a protein unfolded to some degree.

"Refolding" refers to the return of the conformation of a solubilized protein to a conformation such that the protein exhibits its biological activity.

"Optimal dilution level" refers to the concentration level of solubilizing agent in a given solubilized protein solution at which the protein's conformation factors reassert themselves, causing the protein to refold.

"Ideal mixing" refers to conditions resulting in a homogenous solution without substantial concentration gradients in solution. Ideal mixing conditions are a function of a solution's "mixing time".

"Mixing time" is the time needed for the molecules in a droplet added to a solution to be dispersed evenly throughout the solution.

The present invention provides a method for treating solubilized proteins, permitting continuous and efficient refolding of the proteins to a biologically active conformation. The process of the invention provides the protein in a stable conformation exhibiting its characteristic biological activity.

The initial step of this invention involves adjusting the protein concentration of a solubilized protein solution to minimize reaggregation of the solubilized protein upon dilution. If the protein concentration is too high at the optimal dilution level, when the solubilizing agent ceases to have an effect and the protein begins to refold, the protein will begin to reaggregate to other proteins and to solution contaminants. The protein concentration desired at the optimal dilution level for a given protein is easily determined by those skilled in the art by measuring the concentration of refolded protein in a series of solubilized protein solutions diluted to varying concentrations above and below the optimal dilution level, and determining the protein concentration at which optimal refolding is obtaining. Any standard protein measurement techniques can be used to determine the protein concentration, such as biological assays, optical density measurements at 280 nm., Lowry, Biuret or Biorad methods, or immunoassay methodologies. The solubilized protein solution is typically diluted to the desired protein concentration with a buffer containing the solubilzing agent.

For example, in the case of IFN-$\gamma$, it has been found that the concentration of solubilized IFN-$\gamma$ in the solution must first be adjusted to between approximately 1 to 10 mg/ml in order to achieve a satisfactory recovery of soluble, biologically active IFN-$\gamma$ upon dilution. A higher concentration promotes electrostatic interactions between the monomers upon dilution of the solubilizing agent, which interferes with the refolding and the solubility of the protein.

If the desired protein is in the form of an insoluble aggregate, the protein is treated as discussed on pages 2-3, supra, to obtain the solubilized protein solution, which is then adjusted to the desired protein concentration.

The refolding of the solubilized protein is accomplished by rapidly diluting the solubilized protein solution in a small volume continuous flow reaction vessel while maximizing ideal mixing conditions, resulting in a net reduction of the solubilizing agent concentration to below the optimal dilution level. Once this optimal dilution level is reached, the individual protein monomers begin to refold to a stable biologically active conformation. The refolding time varies with the protein, and for IFN-$\gamma$ takes about 15 minutes. The continuous flow reaction vessel is operated to maintain the protein in the reactor for the necessary time for refolding to occur.

The reaction vessel typically consists of a mixing chamber, a means for vigorous mixing, a temperature control device, a feedback device controlling the flow rate of solubilized protein solution into the mixing chamber, a device controlling diluent flow into the mixing chamber, and a control for maintaining a constant volume in the mixing chamber.

We utilize a small volume mixing chamber for diluting the protein solution, approximately 25 liters in volume for a production process starting with 500 liters of solubilized protein solution. In a small reaction vessel, there is less distance for a molecule to travel, so the mixing time will be lower than in a large reaction vessel. The size of the mixing chamber can be scaled up to accommodate large volume purification processes while maximizing ideal mixing conditions. Thus, for example, for a production process starting with 5000 liters of solubilized protein solution, a mixing chamber of 250 liters would be used.

In a small volume of solution subjected to vigorous mixing, the mixing time will be substantially instantaneous, within a matter of seconds. Thus, with this small volume mixing chamber, it is possible to provide vigorous mixing such that a homogenous solution is rapidly obtained upon mixing the solubilized protein solution with diluent. This avoids the formation of concentration gradients, thus allowing the use of deionized water as diluent, as well as providing repeatable process performance from run to run and increasing the yield of properly refolded protein.

Thus, according to the method of this invention, after the solubilized protein has been diluted to a predetermined protein concentration, it is fed continuously into a mixing chamber into which the diluent is pumped at a specific rate calculated to decrease the concentration of the solubilizing agent to the optimal dilution level. Because of the small volume of the stirred tank reactor, the solubilized protein solution and diluent are mixed instantaneously.

The diluent used can include a variety of buffer solutions, but most preferably the diluent used herein is deionized water. The method of dilution disclosed in this invention unexpectedly allows the use of water as a diluent, probably because the dilution method minimizes ionic strength and pH gradients in solution. Additionally, because the addition of deionized water will decrease the overall solution ionic strength, unwanted interactions may be further reduced, possibly resulting in an enhanced yield of refolded protein.

Because the extent to which the solubilized protein solution is diluted directly affects the refolding process, as discussed above, the optimal dilution level must be continuously maintained. This is accomplished as follows. First, the extent to which the solubilized protein in the mixing chamber has been refolded is monitored by, e.g., monitoring the protein concentration, the diluent flow rate or the solution conductivity. Preferably, the extent of protein refolding is monitored continuously by monitoring solution conductivity, with the conductivity being controlled by a feedback control loop to precisely maintain optimal refolding conditions. By operating the reactor at a continuous diluent flow rate, the conductivity controller provides the proper feed rate of solubilized protein solution to the mixing chamber to maintain a predetermined conductivity.

This conductivity is that at which optimum protein refolding occurs, and can easily be determined by one skilled in the art by measuring the conductivity of a protein solution containing properly refolded protein in the same solution at the same pH, temperature and concentration as the solution being used in the dilution process. The control system continuously monitors the conductivity of the protein solution in the reactor and is used to activate a pump which feeds the solubilized protein solution into the mixing chamber.

The protein solution is allowed to remain in the mixing chamber for the period calculated to be the time at which refolding is complete. For IFN-γ this period is 15 minutes. The outlet from the mixing chamber provides a steady continuous flow of fluid containing soluble, refolded protein which may be further purified and concentrated by conventional means.

Finally, although the above discussion makes specific reference to IFN-γ, many other proteins, such as, e.g., those listed at page 7, supra, can be refolded using the method disclosed herein, and the foregoing discussion and following example should not be interpreted as limiting the scope of this invention to a process for refolding IFN-γ or any particular protein.

In order that this invention may be more fully understood, the following illustrative example is set forth.

EXAMPLE 120 grams of a membrane pellet containing IFN-γ with a purity of 74% monomer and 10% dimer was obtained using conventional techniques. The IFN-γ is present in the pellet in the form of insoluble aggregates. The pellet was solubilized according to conventional techniques to yield a volume of 10.0 L of 4.5 M urea extract at pH 6.25 at room temperature.

Refolding Procedure

To begin the refolding process, 400 ml of the 4.5 M extract as obtained above was added to 3600 ml of cold deionized water (DI H₂O), in a 4.0 Liter continuous stirred tank reactor (CSTR). The conductivity was measured with a conductivity controller probe such as an Aqua Purometer obtainable from McNabb, Inc., and the adjustable set point was adjusted to a conductivity value characteristic of the refolded protein in the same solution conditions being used in the refolding step. The CSTR was kept stirring on a magnetic stir plate, at a low enough rate to prevent vortexing and the subsequent entraining of air within the solution.

The flow rate on a peristalic pump was set to ~270 ml/minute, which pumped cold DI H₂O into the CSTR from a 90 L reservoir. Another peristaltic pump was set to ~40 ml/minute and plugged into the conductivity controller so as to pump the 4.5 M extract into the CSTR whenever the conductivity fell below the set point. Total flow rate out of the stirred tank was 300 ml/minute, resulting in an average residence time of ~15 minutes which was calculated to be the time needed for optimum protein refolding. The refolded protein solution was removed from the CSTR through an overflow port at the 4 L level and collected in a 2×50 L holding vessel.

The refolded protein solution was clarified through a 0.22 Mm filter at 300 ml/minute from the holding vessel after ~1 L of overflow was collected. The yield and biological activity of properly folded IFN-γ was measured by standard protein and antiviral assays, respectively.

While a number of embodiments of this invention are presented hereinabove, it will be apparent to a person skilled in this art that the basic disclosures herein can be altered to provide other embodiments which utilize the process of this invention. Therefore, it will be appreciated that the scope of this invention is intended to encompass all such obvious variations of the specific embodiments which have been presented hereinabove, and all such embodiments and equivalents are contemplated within the invention as defined in the apended claims.

We claim:

1. A process for treating a solubilized protein to obtain the protein in a properly folded, bioligically active conformation, the protein being selected from the group consisting of insulin, proinsulin, bovine, pancreatic ribonuclease, lysozyme, bovine pancreatic trypsin inhibitor, gamma interferon and other interferons, rennin, plasminogen activator, prolactin, human α-1 trypsin inhibitor, and Factor VIII, said process comprising the steps of:
    (a) continuously feeding a solution of the solubilized protein concurrently with a diluent consisting essentially of water into a continuous flow reaction vessel under ideal mixing conditions which yield homogenous solutions without concentration gradients, in a ratio such that the concentration of the solublizing agent in the solubilized protein solution is diluted below an optimal dilution level wherein the solubilizing agent ceases to affect the conformation of the protein and the protein begins to refold into a biologically active conformation, and
    (b) continuously removing the protein solution from the vessel at a flow rate such that the average residence time of the protein in the vessel is sufficient for optimum protein refolding.

2. The process according to claim 1 wherein the ratio of diluent to solubilized protein solution is controlled by:
    (a) operating the mixing chamber at a continuous diluent flow rate,
    (b) continuously monitoring the extent to which the protein in the mixing chamber is refolded, and
    (c) maintaining the ratio of diluent to solubilized protein solution at the optical dilution level in the mixing chamber by feeding in the solubilized protein solution.

3. The process according to claim 1, wherein the ratio of diluent to solubilized protein solution is controlled by:
    (a) operating the mixing chamber at a continuous diluent flow rate,
    (b) continuously monitoring the conductivity of the solution in the mixing chamber, and
    (c) maintaining the conductivity of the solution in the mixing chamber at a predetermined set point at which optimum protein refolding occurs by feeding in the solubilized protein solution when the conductivity of the solution in the mixing chamber decreases beyond the set point.

4. The process according to claim 1, 2 or 3, wherein the diluent is deionized water.

5. The process according to claim 1, 2 or 3, wherein the protein is solubilized with a solubilizing agent, selected from the group consisting of guanidine hydrochloride, urea or sodium dodecyl sulfate or mixtures thereof, and optionally a reductant, or mixtures thereof.

6. A process for treating a solubilized protein consisting of human gamma interferon to obtain the protein in a properly folded, biologically active conformation, comprising the steps of:

(a) continuously feeding a solution of the solubilized protein concurrently with a diluent consisting essentially of water into a continuous flow reaction vessel under ideal mixing conditions which yield homogenous solutions without concentration gradients, in a ratio such that the concentration of the solubilizing agent in the solubilized protein solution is diluted below an optimal dilution level wherein the solubilizing agent ceases to affect the conformation of the protein and the protein beings to refold into a biologically active conformation, and (b) continuously removing the protein solution from the vessel at a flow rate such that the average residence time of the protein in the vessel is sufficient for optimum protein refolding.

7. The process according to claim 6 wherein the ratio of diluent to solubilized protein solution is controlled by:

(a) operating the mixing chamber at a continuous diluent flow rate, (b) continuously monitoring the extent to which the protein in the mixing chamber is refolded, (c) maintaining the ratio of diluent to solubilized protein solution at the optimal dilution level in the mixing chamber by feeding in the solubilized protein solution.

8. The process according to claim 6 wherein the ratio of diluent to solubilized protein solution is controlled by:

(a) operating the mixing chamber at a continuous diluent flow rate, (b) continuously monitoring the conductivity of the solution in the mixing chamber, and (c) maintaining the conductivity of the solution in the mixing chamber at a predetermined set point at which optimum protein refolding occurs by feeding in the solubilized protein solution when the conductivity of the solution in the mixing chamber decreases beyond the set point.

9. The processes according to claims 6, 2 or 3 wherein the diluent is deionized water.

10. The processes according to claims 6, 2 or 3 wherein the protein is solubilized with a solubilizing agent, selected from the group consisting of guanidine hydrochloride, urea or sodium dodecyl sulfate or mixtures thereof, and optionally a reductant, or mixtures thereof.

* * * * *